United States Patent [19]
Rajan et al.

[11] Patent Number: 5,906,578
[45] Date of Patent: May 25, 1999

[54] METHOD AND SYSTEM FOR PROBE POSITIONING IN TRANSESOPHAGEAL ECHOCARDIOGRAPHY

[76] Inventors: Govinda N. Rajan, Goudsesingel 37F, Rotterdam, Netherlands, 3031 EC; Ravi Subramanian, 89 Washington Pl., Apt. #3M, New York, N.Y. 10011; Valavanur A. Subramanian, 333 E. 69th St., Apt. #11C, New York, N.Y. 10021

[21] Appl. No.: 08/877,608

[22] Filed: Jun. 18, 1997

[51] Int. Cl.$^6$ ................................ A61B 5/00; A61B 8/00
[52] U.S. Cl. ............................................ 600/424; 600/463
[58] Field of Search .................................... 600/426, 437, 600/424, 463; 382/113, 278

[56] References Cited

U.S. PATENT DOCUMENTS

| | | | |
|---|---|---|---|
| 4,270,143 | 5/1981 | Morris | 364/516 |
| 5,181,513 | 1/1993 | Touboul et al. | 600/443 |
| 5,291,889 | 3/1994 | Kenet et al. | 600/476 X |
| 5,381,791 | 1/1995 | Qian | 600/426 X |
| 5,398,691 | 3/1995 | Martin et al. | 600/437 X |
| 5,400,771 | 3/1995 | Pirak et al. | 128/207.14 |
| 5,434,617 | 7/1995 | Bianchi | 348/170 |
| 5,572,999 | 11/1996 | Funda et al. | 600/118 |
| 5,631,970 | 5/1997 | Hsu | 382/113 |
| 5,631,981 | 5/1997 | Rao | 382/228 |
| 5,638,819 | 6/1997 | Manwaring et al. | 600/424 |
| 5,690,108 | 11/1997 | Chakeres | 606/130 |
| 5,765,561 | 6/1998 | Chen et al. | 348/77 |

*Primary Examiner*—Francis J. Jaworski
*Attorney, Agent, or Firm*—Pennie & Edmonds LLP

[57] ABSTRACT

A method of optimally positioning an imaging device comprising the steps of storing a reference image; continuously obtaining an acquired view with the imaging device; determining whether the imaging device is in an optimal position by periodically comparing the acquired image with the reference image; and adjusting the position of the imaging device if the imaging device is not in an optimal position.

11 Claims, 6 Drawing Sheets

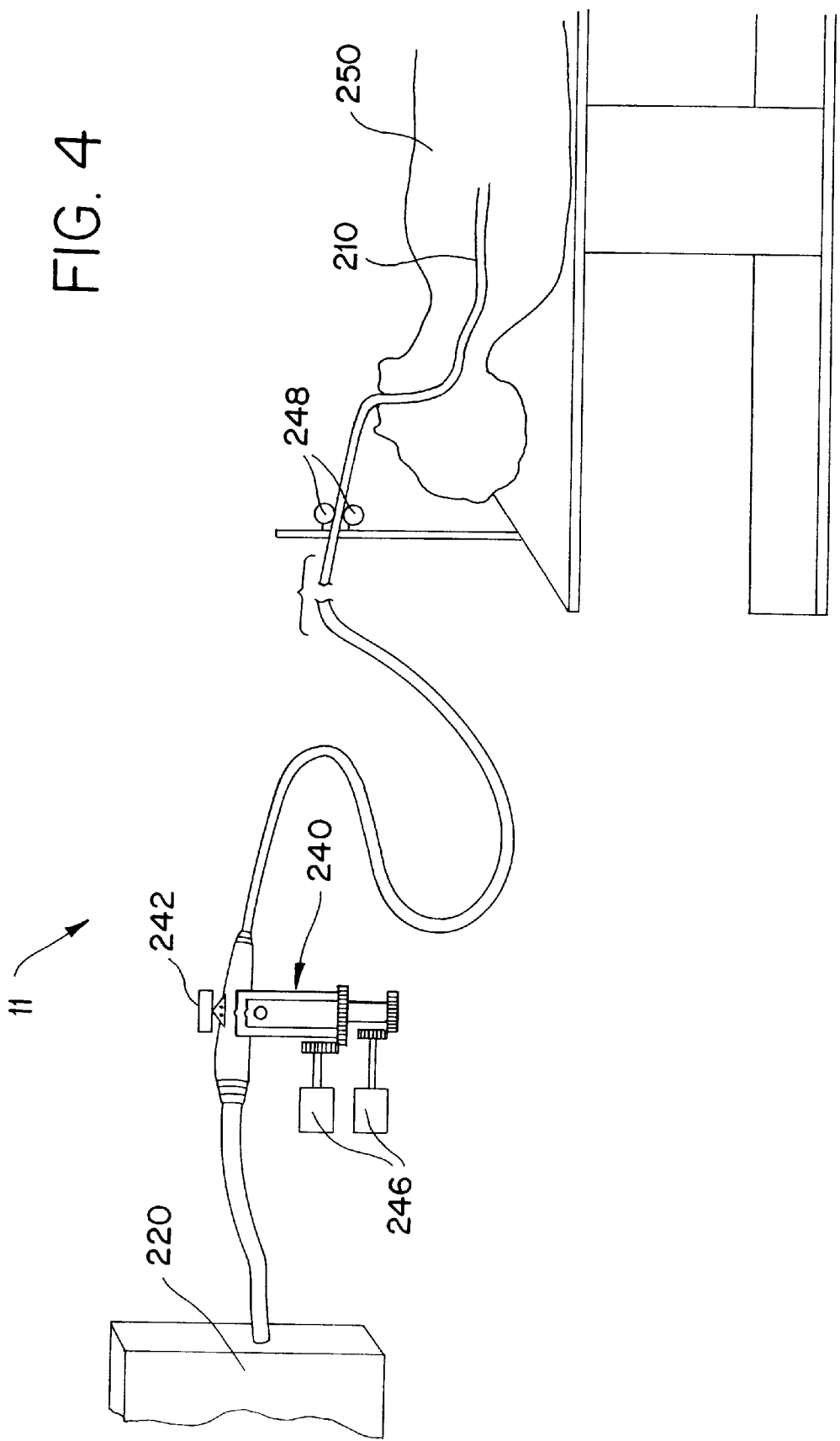

FIG. 7b
FIG. 7a
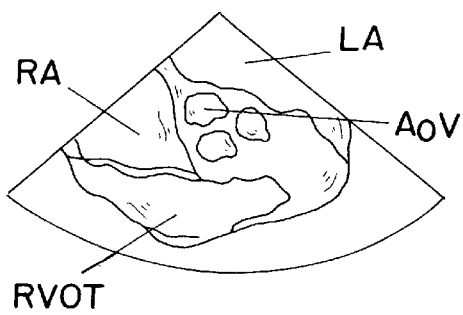
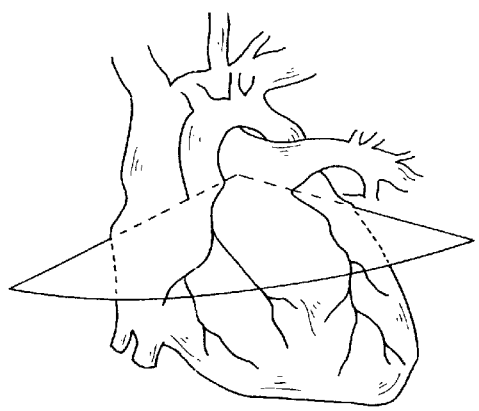
FIG. 8b
FIG. 8a
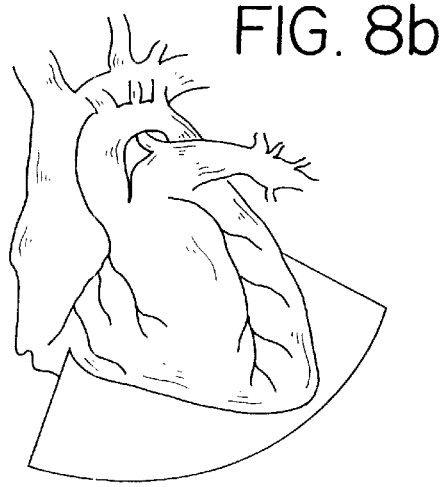
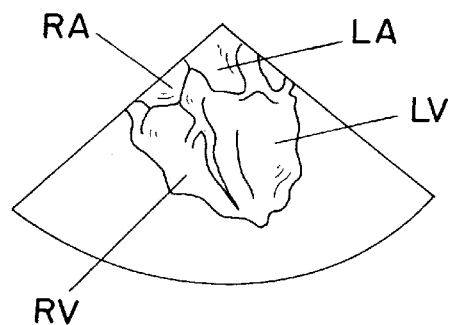
FIG. 9b
FIG. 9a
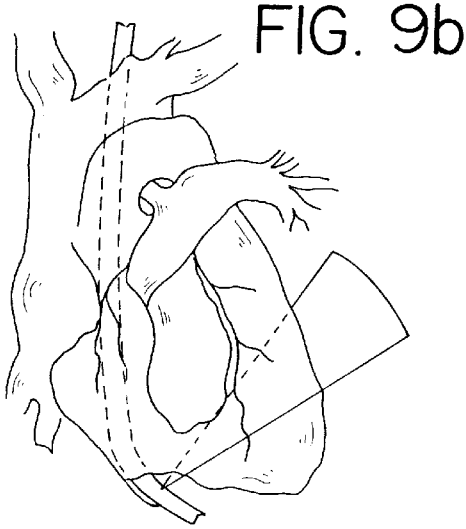
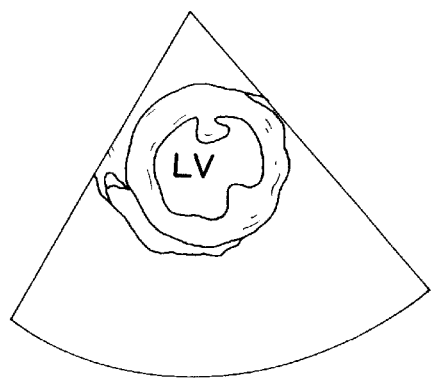

METHOD AND SYSTEM FOR PROBE POSITIONING IN TRANSESOPHAGEAL ECHOCARDIOGRAPHY

FIELD OF INVENTION

This invention relates to a system and method of continuous monitoring of the position of a probe or sensor during medical procedures such as transesophageal echocardiography.

BACKGROUND OF INVENTION

Echocardiography is the use of ultrasound in the investigation of the heart and great vessels and diagnosis of cardiovascular lesions, and in transesophageal echocardiography (TEE), the ultrasonic record is obtained from a miniaturized transducer swallowed by a patient to predetermined distances in the esophagus and stomach.

TEE is a popular diagnostic procedure which is being used at ever-increasing numbers of medical centers worldwide. The quality of the image obtained during this procedure is a critical factor in obtaining accurate diagnoses, and the most important factor in obtaining quality images continuously is the positioning of the ultrasound sensor or transducer.

The transducer is typically mounted at the tip of the endoscope which is inserted through the mouth of the patient into the esophagus. This transducer is connected to imaging electronics, which then displays internal images of the patient on a screen.

Positioning systems for endoscope ultrasound probes are known. For example, U.S. Pat. No. 5,181,514 to Solomon et al. discloses a motorized positioning system which provides for automated control of an ultrasound transducer device. In this device, a switch mechanism is manipulated to provide power to actuate a motor which is mechanically coupled to the device. The device may be rotated to any angular position to provide a variety of scan planes for obtaining a plurality of corresponding two-dimensional cross-sectional images.

Methods for guiding medical equipment within the body are also known. For example, U.S. Pat. No. 5,445,144 to Wodicka et al. discloses an apparatus and method for acoustically guiding a distal end of a tube within a body. The method utilizes sound pulses reflected from within the body to guide insertion of the tube within the body.

To obtain a desired internal view with the transducer, the technician or clinician adjusts the endoscope while watching the screen. The technician may adjust the endoscope either by altering the depth of its insertion, rotating it, or tilting it until the desired view appears on the screen. The position of the patient is occasionally changed during the course of procedure such as TEE. As a result, the position of the endoscope changes, and this requires the technician to constantly adjust the endoscope to maintain an optimal view of the procedure. Therefore, the technician must constantly monitor the image on the screen in addition to performing other duties in the operating room or in the clinic.

A need therefore exists in the art for a system which will automate or simplify the task of obtaining a desired internal view of the patient and maintaining this view during positional changes of the patient.

SUMMARY OF INVENTION

The present invention relates to a method of positioning a probe or other imaging device, comprising the steps of storing a first image; acquiring a second image with the optical device; determining whether the probe is in a desired position by comparing the second image with the first image; and positioning the probe if it is not in a desired position to place it in a desired position.

BRIEF DESCRIPTION OF THE DRAWINGS

Reference is next made to a brief description of the drawings, which are intended to illustrate several embodiments of the present invention. The drawings and detailed descriptions which follow are intended to be merely illustrative, and are not intended to limit the scope of the invention as set forth in the appended claims.

FIG. 4 illustrates the probe positioning system including an automatic electrical drive system;

FIG. 7a is a short axis view of the aortic valve taken from the plane depicted in FIG. 7b;

FIG. 8a is a long axis view of the four heart chambers and the mitral valve taken from the plane depicted in FIG. 8b;

FIG. 9a is a mid-papillary short axis view of the mid-ventricle taken from the plane depicted in FIG. 9b;

DETAILED DESCRIPTION

This invention can be used to automatically seek a desired image by comparing an acquired image with either a previously acquired image or a reference image stored in a knowledge base or other equivalent repository. The acquired image is obtained by a sensor mounted on a probe and the comparison between the images determines the appropriate movement, if any, of the probe. The probe is moved either automatically or by a user who is given a signal. When the position of the probe has been determined for the desired image, the system continuously monitors the desired image, at preset intervals of time, for accidental movements of the probe.

Figure 1:
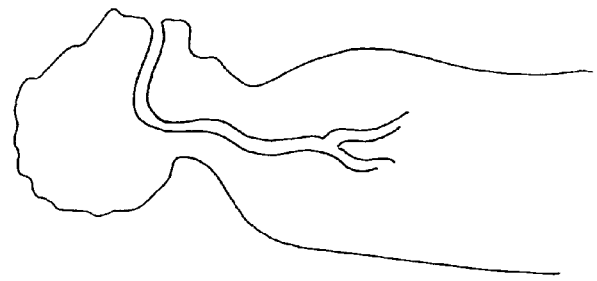
FIG. 1 illustrates tilting of an endoscope inserted within the esophagus about an axis perpendicular to the plane of the paper.

As explained above in the context of TEE, a miniaturized transducer is mounted at the tip of an endoscope, and this probe, which comprises both the endoscope and transducer, is swallowed by the patient into the esophagus. The image acquired by the transducer depends on the depth of insertion of the probe, the rotation of the probe, and the tilt of the probe. The tilt of the probe about an axis perpendicular to the plane of the paper is shown in FIG. 1. The probe also may be tiled about different axes such as an axis parallel to the plane of the paper.

Figure 2:
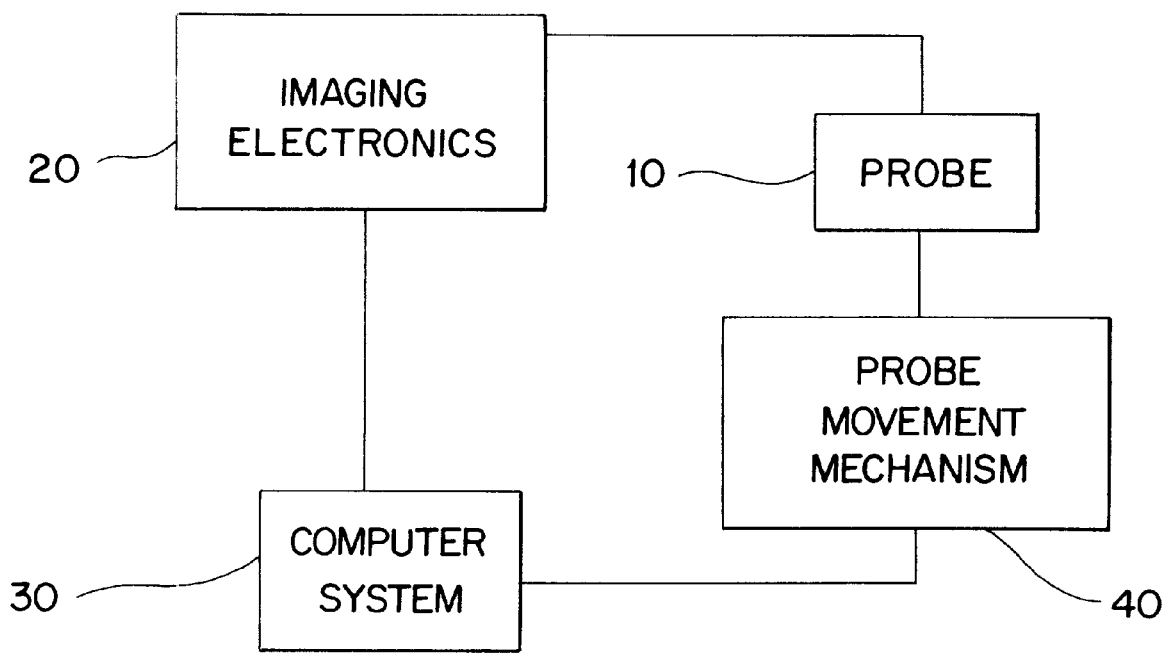
FIG. 2 is a block diagram of the probe positioning system with automatic probe adjustment.

As illustrated in FIG. 2, the probe positioning system 5 comprises probe 10, imaging electronics 20, computer system 30, and probe movement mechanism 40. Probe 10 acquires image data which is then composed by imaging electronics 20. Computer system 30 compares this image with a stored or reference image, then automatically adjusts probe 10 by means of probe movement mechanism 40. Probe 10 does not require adjustment once the desired image has been obtained. This sequence of steps is repeated to maintain the desired image. The individual components of system 5 are known in the art.

Figure 3:
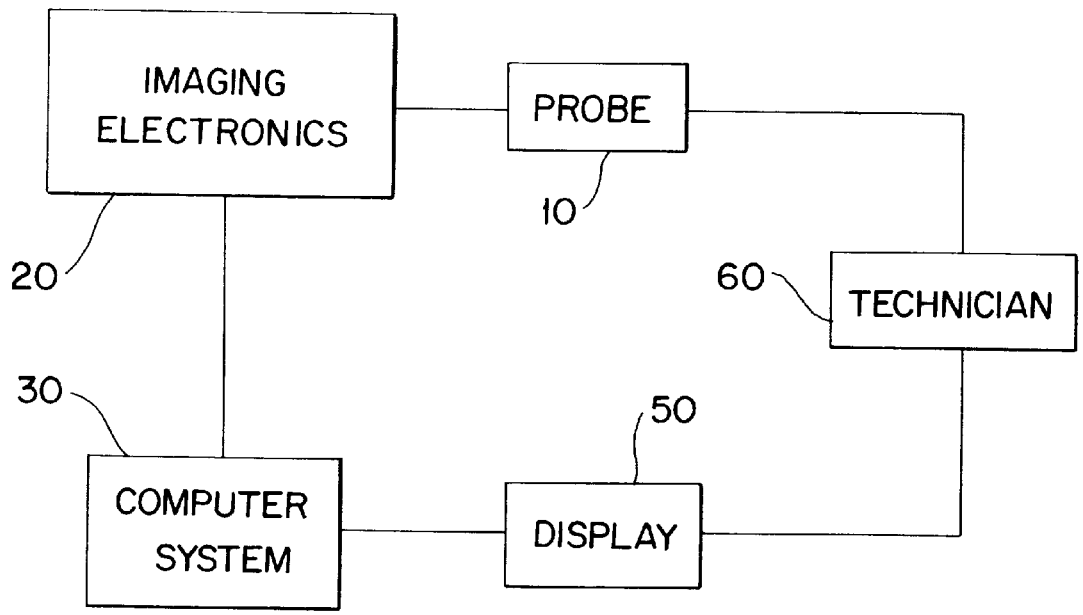
FIG. 3 is a block diagram of the probe positioning system without automatic probe adjustment.

An alternative system 8 is illustrated in FIG. 3. System 8 also comprises probe 10, imaging electronics 20, and computer system 30. In addition, in lieu of probe movement mechanism 40, system 8 comprises display 50 and technician 60. Probe 10 acquires image data which is then composed by imaging electronics 20. Computer system 30 compares this image with a stored or reference image, then a signal from display 50 instructs technician 60 on whether and how to adjust probe 10. The technician does not need to adjust probe 10 once the desired image is obtained, and this sequence of steps is repeated to maintain the desired image. The individual components of system 8 are also known in the art.

The probe positioning system of the present invention may include an automatic electrical drive system as illustrated in FIG. 4. In this system 11, imaging electronics 220 is electrically connected to probe movement mechanism 240 which in turn electronically drives probe 210. Probe movement mechanism 240 comprises two electrical switches 242, two knobs 246, and a set of rollers 248. The two knobs 246 are provided for tilting probe 210, and these may be driven by a motor, such as a stepper motor and a set of gears. Electrical switches 242 may be manually adjusted, or they may be adapted to receive electrical signals from a computer system. Rollers 248 are attached to a stand near the patient and are used to insert or withdraw probe 210 into or from the patient 250.

Figure 5:
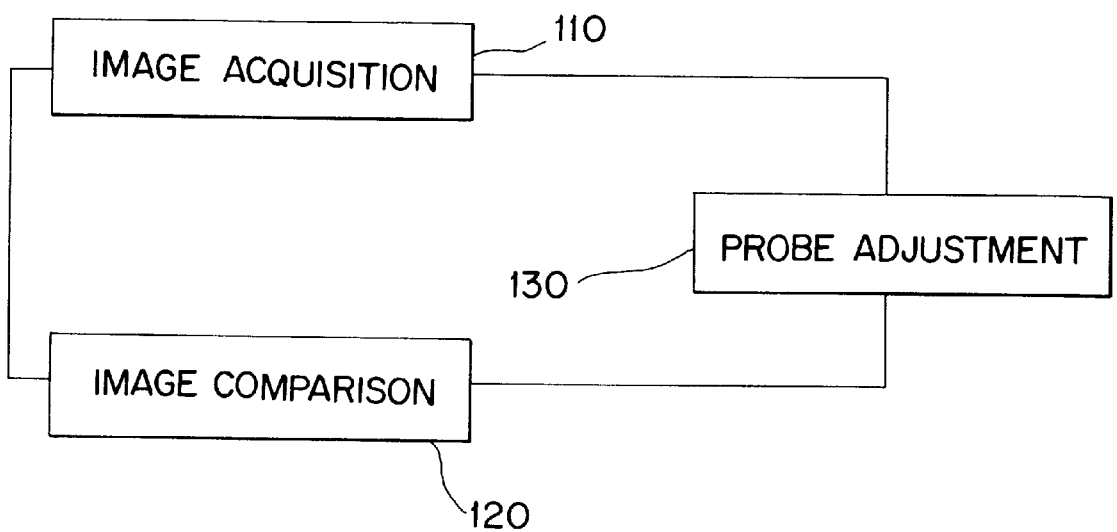
FIG. 5 is a flow chart depicting the steps in probe positioning.

The sequence of steps of probe positioning is illustrated in FIG. 5. There are three basic steps, including image acquisition step 110, image comparison step 120, and probe adjustment step 130. The results of image comparison step 120 determines whether or not probe adjustment step 130 is necessary. These steps are repeated throughout the procedure or as long as an internal image of the patient is required.

Figure 6:
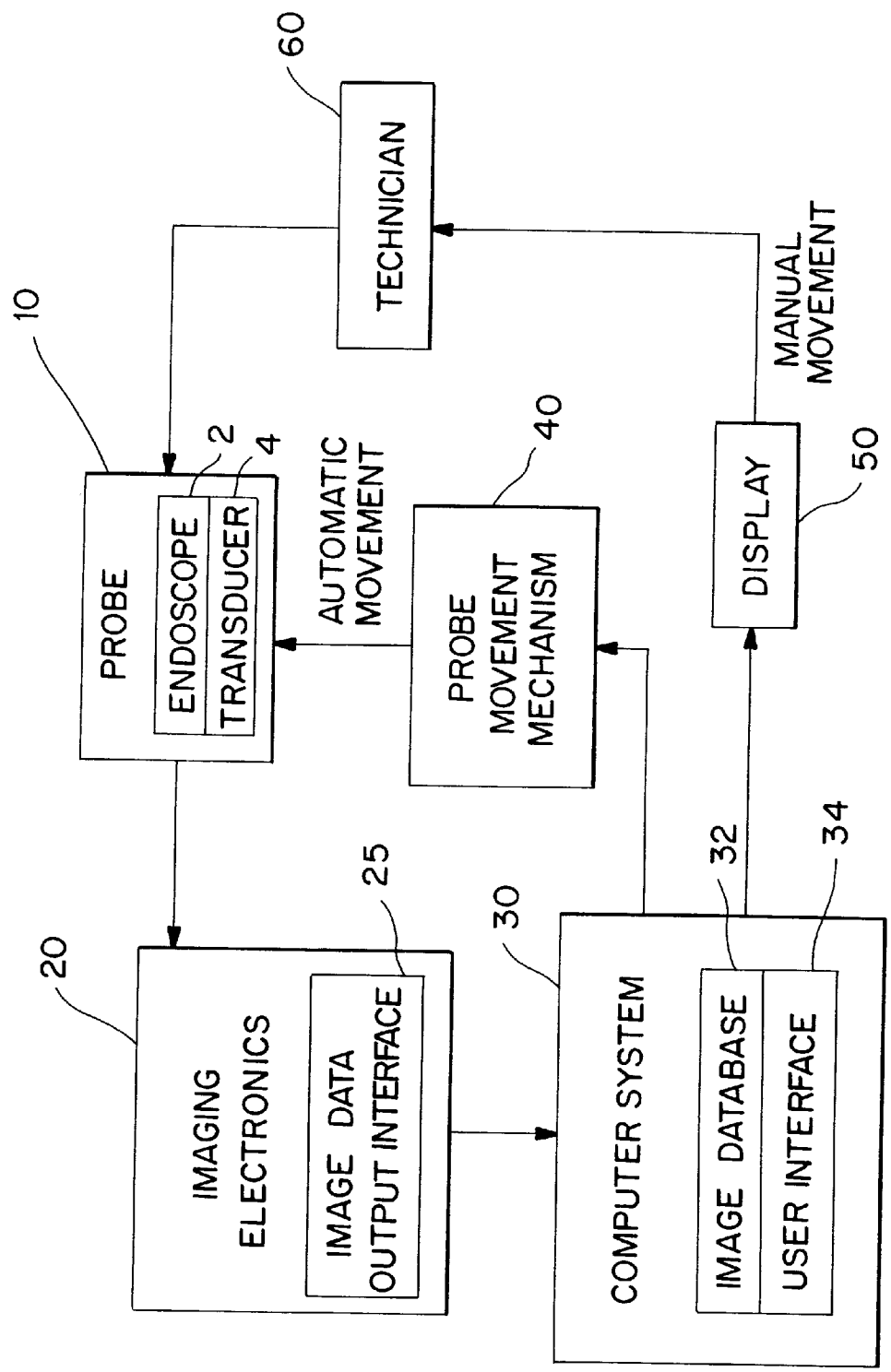
FIG. 6 is a more detailed block diagram of the probe positioning system with and without automatic probe adjustment.

As illustrated in more detail in the block diagram of FIG. 6, probe 10 comprises an endoscope 2 and a miniaturized transducer 4 mounted at the tip of the endoscope 2. Probe 10 acquires image data and sends this data to imaging electronics 20, which then composes the acquired image. Imaging electronics 20 is equipped with image data output interface 25, which produces an image output. Known imaging electronics systems are usually equipped with an image data output interface. The image output, which may be either analog or digital, is input into computer system 30, and computer system 30 compares this image output with a reference or stored image. The stored image may be compressed or uncompressed.

A signal or message is then conveyed by the display 50. This message may comprise simple text, which may, for example, instruct technician 60 on whether to adjust probe 10 or how to adjust probe 10 in order to obtain an acquired image which more closely matches the stored image. Alternatively, the message may comprise graphical means such as computer graphics. Technician 60 may then manually adjust probe 10, if necessary, to obtain the desired or optimal image.

In the alternative embodiment illustrated in FIGS. 2 and 6, the computer system 30 controls probe movement mechanism 40 which automatically adjusts probe 10 in order to obtain a desired image.

The computer system 30 comprises means for storing image data or image characteristics for various internal images or views of the patient within a database 32. A database of image data can be collected initially and classified by expert technicians. In addition, the reference or stored image may be obtained from the patient himself, either from a previous procedure or as part of the preparation for the present procedure. Alternatively, a desired image may be scanned into the computer and used as the reference image. This database can be a collection of bitmap images or vectorized images or can be embedded as trained data in a neural network or as a set of rules in a rule based or fuzzy logic expert system. In addition to image data, the database also contains data regarding the approximate position of the probe for each internal view, data regarding the cardiac cycle (e.g., diastolic, systolic, etc.), and data regarding characteristics or dimensions of each view (e.g., minimal area, maximal area, etc.). The computer system 30 shall also include a user interface 34 which allows the user to update image database 32 whenever necessary, even while the system 30 is in use, so that additional updated views can be added online.

In addition, the computer system 30 may store more than one reference image, and probe 10 may be adjusted to obtain more than one desired or optimal image, each desired image corresponding to a reference image. Probe 10 may then be adjusted, either manually or automatically, to alternate between various positions in order to obtain alternating desired images. This is useful in cases when different parameters or dimensions of the patient need to be continuously monitored throughout the course of a procedure and when different internal views are required to obtain the various parameters. These parameters may be calculated by computer system 30.

Some of the most commonly used views of the heart and their approximate position characteristics include the following.

1. Aortic valve short axis, 28–32 cm from incisors, transverse and 25–40° orientation of probe (with 0° measured in the horizontal position) (see FIGS. 7*a* and 7*b*). This image is used to detect aortic stenosis.

2. Four chamber long axis view for mitral valve, 29–33 cm from incisors, transverse and 0° orientation of probe (see FIGS. 8*a* and 8*b*). This image is used to detect right ventricle dysfunction.

3. Mid-papillary short axis view for mid-ventricle, 38–42 cm from incisors, transverse and 0–15° orientation of probe (see FIGS. 9*a* and 9*b*). This view is used to monitor filling of the left ventricle and area ejection fraction.

SPECIFIC EMBODIMENTS

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

As an illustrative example, we will now describe the method for obtaining the short axis view of the left ventricle (viewed from the apex to the base of the heart). The required view of the heart is shown in FIG. 9 which shows a complete view of the left ventricle (LV) and a partial view of the right ventricle (RV). This view of the heart is used to monitor the left ventricle and the myocardium. Specifically, this view is used, inter alia, to measure the area ejection fraction and to detect problems such as ischemia. This image is stored in a database as the stored or reference image.

The short axis view of the left ventricle is obtained when the endoscope tip is about 400 mm from the incisors. A physician introduces the endoscope into the esophagus through the mouth of the patient and inserts it to about 250 mm from the incisors. Probe movement mechanism 40 may then be switched on. In this example, probe movement mechanism 40 comprises an automatic electro-mechanical drive mechanism. However, various other types of automatic drive mechanisms may be used and are known in the art.

Figure 10:
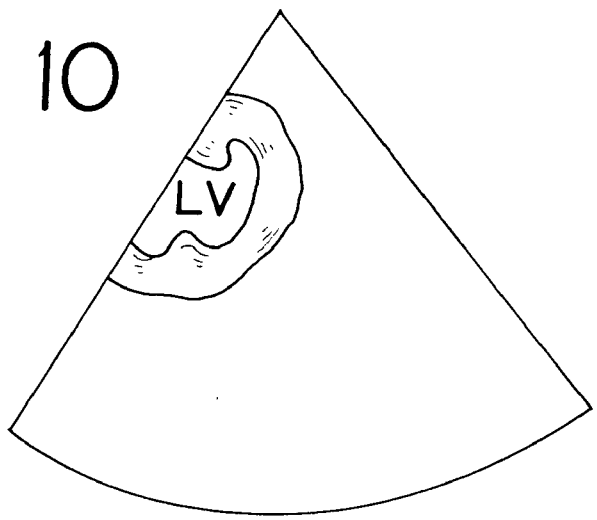
FIG. 10 illustrates an image acquired by the probe positioning system of the present invention.

Computer system 30 includes a user-interface menu by which the physician may enter the desired image, i.e., the short axis view of the left ventricle. A database in computer system 30 then provides the approximate position of the probe required to obtain the short axis view of the left ventricle of the patient. Probe movement mechanism 40 then moves probe 10 to that approximate position. The image illustrated in FIG. 10 is thus obtained by imaging electronics 20. This corresponds to image acquisition step 110 in FIG. 5. This figure clearly shows approximately 50% of the left ventricle.

Computer system 30 also includes an image comparison module which compares the acquired image in FIG. 10 with the reference image in FIG. 9 and detects similarities between the two images. This corresponds to image comparison step 120 in FIG. 5. Structures such as other organs in the patient's body, which are beyond the probe's field of view, are not picked up by probe 10, and therefore do not figure into image comparison step 120. Alternatively, image comparison step 120 can be programmed to ignore extraneous or unneeded structures within the probe's field of view. Because the acquired image is not sufficiently similar to the reference image, computer system 30 instructs probe movement mechanism 40 to adjust probe 10. This corresponds to probe adjustment step 130 in FIG. 5. Computer system 30 stores information regarding previous positions of probe 10 and previous comparisons between the acquired image and the reference image and uses this information to determine the amount and degree of the subsequent adjustment. Once probe 10 has been adjusted, the position coordinates are stored in computer system 30, and image acquisition step 110 is then repeated and a new image is obtained for comparison. This new acquired image is illustrated in FIG. 11.

Figure 11:
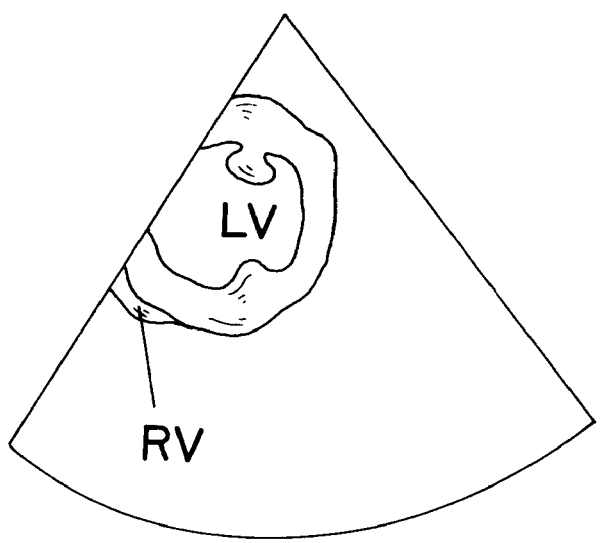
FIG. 11 illustrates another image acquired by the probe positioning system of the present invention.

Image comparison step 120 is then repeated, in which the acquired image in FIG. 11 is compared with the reference image in FIG. 9 and computer system 30 detects approximately 70% similarity. Based on stored position coordinates and the increasing similarity between the two images, the previous adjustment is determined to have been appropriate and the direction of further adjustment may be determined. For example, if probe 10 was inserted further into the esophagus to obtain the acquired image in FIG. 11, subsequent adjustment will comprise even further insertion.

These steps are repeated until the degree of similarity reaches an acceptable level. This level can be pre-programmed or set by the user. Computer system 30 may also be programmed to "remember" the optimal probe position, which is the position of probe 10 corresponding to the highest degree of similarity, above the acceptable level, between the acquired image and the reference image. As long as an acceptable degree of similarity is maintained, probe 10 does not require further adjustment. However, probe positioning system 5 continues to monitor probe 10 in order to maintain the desired or optimal image. In other words, image acquisition step 110 and image comparison step 120 are repeated throughout the procedure, bypassing probe adjustment step 130 as shown in FIG. 5.

If at any time, and for any reason, the degree of similarity drops beneath the acceptable level, probe adjustment step 130 is repeated and probe 10 is adjusted. Probe 10 may be moved to a position corresponding to the acceptable level of similarity. Alternatively, probe 10 may be moved to the optimal probe position. Probe adjustment step 130 is repeated until an acceptable degree of similarity is again obtained. In this way, probe positioning system 5 continuously monitors the acquired image and adjusts probe 10 if necessary.

Probe positioning system 5 also may include a means for user intervention. The user may confirm that probe 10 is optimally positioned by visually checking the acquired image for himself. In addition, the user may wish to adjust the acceptable level of similarity during the course of the procedure. Also, the user may wish to override the system altogether and adjust probe 10 according to his own needs.

Image comparison step 120 may be achieved using a variety of alternative techniques known in the art. Individual pixel representations of the two images may be compared; however, this method is usually slow. Other techniques include comparison of vectorized images, neural network techniques, or comparisons may be made according to rule based or fuzzy logic expert systems. With each of these known comparison techniques, there is an established method of determining the relative quality of the match. Therefore, those with skill in the art can determine the acceptable level of similarity for this method.

It will be readily apparent to those in the art that variations of this method are possible which fall within the scope of the appended claims. As an example, the specific embodiment was described in the context of TEE. However, this method may be used in any medical procedure in which a continuous image of the patient is required.

What is claimed is:

1. A method of obtaining a desired image of a patient with an imaging device, comprising:
   positioning the imaging device;
   continuously obtaining an acquired view comprising a video image of the patient with the imaging device;
   periodically comparing the acquired view with the desired image using an automatic, not manual, technique; and
   adjusting the position of the imaging device if the acquired view is not substantially similar to the desired image.

2. A method of optimally positioning a probe during transesophageal cardiography, comprising:
   storing a reference image;
   positioning a probe within a patient's esophagus;
   continuously obtaining an acquired view of the patient's heart with the probe, wherein the acquired view comprises a video image;
   determining whether the imaging device is in an optimal position by periodically comparing the acquired image with the reference image; and
   periodically adjusting the position of the imaging device if the imaging device is not in an optimal position.

3. A method of optimally positioning an imaging device, comprising:

obtaining a database of reference images taken from a plurality of patients with a probe, wherein the database is saved in an artificial intelligence module;

continuously obtaining an acquired view of a patient with the imaging device;

determining whether the imaging device is in an optimal position by periodically comparing the acquired image with at least one reference image from the database; and adjusting the position of the imaging device if the imaging device is not in an optimal position.

4. The method of claim 3, wherein the artificial module comprises a neural network.

5. The method of claim 3, wherein the artificial module comprises a rule based expert system.

6. The method of claim 3, wherein the artificial module comprises a fuzzy logic expert system.

7. The method of claim 3, wherein the database includes data regarding the approximate position of the probe for obtaining at least one of the reference images.

8. A method of optimally positioning an imaging device for obtaining a desired image of a patient, comprising:

storing at least one reference image;

continuously obtaining an acquired image comprising a video image of the patient with the imaging device;

determining whether the imaging device is in an optimal position by periodically comparing the acquired image with at least one stored reference image using neural network techniques; and adjusting the position of the imaging device if the imaging device is not in an optimal position.

9. A method of optimally positioning an imaging device to obtain a desired image of a patient, comprising:

storing at least one reference image;

continuously obtaining an acquired image comprising a video image of the patient with the imaging device;

determining whether the imaging device is in an optimal position by periodically comparing the acquired image with at least one stored reference image using a rule based expert system; and adjusting the position of the imaging device if the imaging device is not in an optimal position.

10. A method of optimally positioning an imaging device for obtaining a desired image of a patient, comprising:

storing at least one reference image;

continuously obtaining an acquired image comprising a video image of a patient with the imaging device;

determining whether the imaging device is in an optimal position by periodically comparing the acquired image with at least one stored reference image using a fuzzy logic expert system; and adjusting the position of the imaging device if the imaging device is not in an optimal position.

11. A method of optimally positioning an imaging device for obtaining a desired image of a patient, comprising:

sequentially storing a plurality of one reference images;

continuously obtaining an acquired view comprising a video image of the patient with the imaging device;

determining whether the imaging device is in an optimal position by periodically comparing the acquired image with alternating stored reference images using an automatic, not manual, technique; and adjusting the position of the imaging device if the imaging device is not in an optimal position.

* * * * *